United States Patent [19]
Spanton et al.

[11] Patent Number: 5,945,405
[45] Date of Patent: Aug. 31, 1999

[54] CRYSTAL FORM O OF CLARITHROMYCIN

[75] Inventors: Stephen G. Spanton, Green Oaks; Rodger F. Henry, Waukegan, both of Ill.; David A. Riley, Kenosha, Wis.; Jih-Hua Liu, Green Oaks, Ill.

[73] Assignee: Abbott Laboratories, Abbott Park, Ill.

[21] Appl. No.: 08/785,623

[22] Filed: Jan. 17, 1997

[51] Int. Cl.⁶ .............................. A61K 31/70; C07H 1/00; C07H 17/08
[52] U.S. Cl. .............................. 514/29; 536/7.2; 536/18.5
[58] Field of Search ..................................... 536/7.2, 18.5; 514/29

[56] References Cited

U.S. PATENT DOCUMENTS

| | | | |
|---|---|---|---|
| 4,331,803 | 5/1982 | Watanabe et al. | 536/7.2 |
| 4,670,549 | 6/1987 | Morimoto et al. | 536/7.4 |
| 4,672,109 | 6/1987 | Watanabe et al. | 536/72 |
| 4,808,411 | 2/1989 | Lu et al. | 424/441 |
| 4,990,602 | 2/1991 | Morimoto et al | 536/7.3 |
| 5,556,839 | 9/1996 | Greene et al. | 574/29 |

FOREIGN PATENT DOCUMENTS

| | | |
|---|---|---|
| B 260 938 | 9/1992 | European Pat. Off. . |
| 9804573 | 2/1998 | WIPO . |
| 9804574 | 2/1998 | WIPO . |

OTHER PUBLICATIONS

Acta Crystalographica Section C. Crystal Structure Communications, vol. C49, No. 5 (May 1993), pp. 1227–1230, Iwaskai et al., "Structure of 6–O–Methylerythromycin A (Clarithromycin)".

Journal of Antibiotics, vol. XLII, No. 6 (Jun. 1989), pp. 1012–1014, Takashi Adachi et al., "Crystal and Molecular Structure of (14R)–14–Hydroxy–6–O–Methylerythromycin A".

Cremer et al., *Proceed. Intern. Symp. Control. Rel. Bioact. Mater.*, 1995, 22, 732–33.

*Primary Examiner*—Elli Peselev
*Attorney, Agent, or Firm*—Portia Chen; Mona Anand

[57] ABSTRACT

The present invention concerns the novel antiobiotic 6-O-methylerythromycin A form O solvate, a process for its preparation, pharmaceutical compositions comprising this compound and a method of use as a therapeutic agent.

25 Claims, No Drawings

CRYSTAL FORM O OF CLARITHROMYCIN

TECHNICAL FIELD

This invention relates to a compound having therapeutic utility and to a method for its preparation. More particularly, the present invention concerns the novel compound 6-O-methylerythromycin A crystal form 0 solvate, a process for its preparation, pharmaceutical compositions comprising this compound and a method of use as a therapeutic agent.

BACKGROUND OF THE INVENTION

6-O-methylerythromycin A (Clarithromycin) is a semi-synthetic macrolide antibiotic of formula

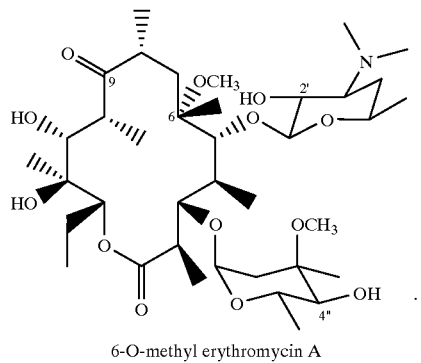

6-O-methyl erythromycin A

Two distinct crystal forms of 6-O-methylerythromycin A, designated "form I" and "form II" have been identified. The crystal forms are identified by their single crystal or powder diffraction patterns.

6-O-methylerythromycin A exhibits excellent antibacterial activity against gram-positive bacteria, some gram-negative bacteria, anaerobic bacteria, Mycoplasma, and Chlamidia. It is stable under acidic conditions and is efficacious when administered orally. It is a useful therapy for infections of the upper respiratory tract in children and adults. 6-O-methylerythromycin A is available as tablets and as an oral suspension. Drugs currently on the market are formulated using the thermodynamically more stable 6-O-methylerythromycin A form II.

The oral suspension is particularly useful for patients such as children and the elderly who have difficulty swallowing the tablets. However, because 6-O-methylerythromycin A has such pronounced bitterness conventional approaches to taste masking failed to produce palatable suspensions. Ultimately, it was discovered that 6-O-methylerythromycin A-carbomer (acrylic acid copolymer) complexes provided particles sufficiently palatable for use in the oral suspension. See U.S. Pat. No. 4,808,411.

The 6-O-methylerythromycin A-carbomer complexes used in the oral suspension are prepared by dispersing 6-O-methylerythromycin A in an organic solvent, preferably ethanol, separately dispersing the carbomer in ethanol, mixing the two solutions to allow formation of the desired reaction product, evaporating most of the solvent and diluting the mixture with water to precipitate the carbomer6-O-methylerythromycin A form 0 solvate complex.

SUMMARY OF THE INVENTION

6-O-methylerythromycin A can exist in a third crystal form, designated "form 0". Form 0, I, and II crystals have an identical spectrum of antibacterial activity. 6-O-methylerythromycin A prepared by the various methods described in the patent literature summarized below, in which the compound is purified by recrystallization from ethanol, result in initial formation of the crystalline form 0-ethanolate. Form 0 solvates are also formed with tetrahydrofuran, isopropanol, and isopropyl acetate. The form 0 solvate is converted to the non solvated form I by removing the solvent from the crystal lattice by drying at a temperature of from about 0° C. to about 50° C. Form 0 is converted to the non-solvated crystal form II by heating under vacuum at a temperature of between about 70° C. and 110° C.

The 6-O-methylerythromycin A-carbomer complexes described above are prepared using 6-O-methylerythromycin A form II. Substantial savings in energy and material handling could be realized by forming the carbomer complexes from 6-O-methylerythromycin A form 0 solvate, thereby eliminating the vacuum drying step required to prepare form II crystals. 6-O-methylerythromycin A form 0 solvate is also a useful intermediate in the preparation of the non-solvated 6-O-methylerythromycin A forms I and II.

Accordingly, the present invention in its principle embodiment provides a novel crystalline antibiotic designated 6-O-methylerythromycin A form 0 solvate having the structure

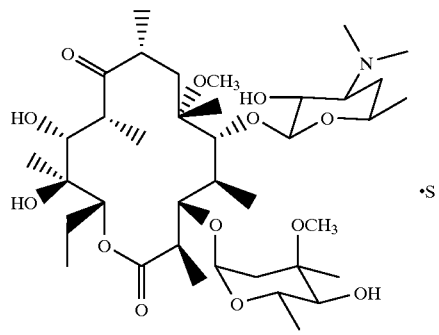

wherein S is a solvating molecule selected from the group consisting of ethanol, isopropyl acetate, isopropanol and tetrahydrofuran.

6-O-methylerythromycin A form 0 solvate is characterized by 2-theta angle positions in the powder x-ray diffraction pattern of 4.581°±0.2, 6.498°±0.2, 7.615°±0.2, 9.169°±0.2, 10.154°±0.2, 11.009°±0.2, 11.618°±0.2, 12.495°±0.2, 13.772°±0.2, 14.820°±0.2, 16.984°±0.2, 18.221°±0.2, 18.914°±0.2 and 19.495°±0.2.

In another embodiment, the present invention provides a composition comprising a therapeutically effective amount of 6-O-methylerythromycin A form 0 solvate in combination with a pharmaceutically acceptable carrier.

In yet another embodiment, the present invention provides a method of treating bacterial infections in a host mammal in need of such treatment comprising administering to the mammal a therapeutically effective amount of 6-O-methylerythromycin A form 0 solvate.

In yet another embodiment, the present invention provides a process for preparing 6-O-methylerythromycin A form 0 solvate comprising (a) converting erythromycin A to 6-O-methylerythromycin A;

(b) treating the 6-O-methylerythromycin A with a solvent selected from the group consisting of (i) ethanol, (ii) isopropyl acetate, (iii) isopropanol, and (iv) tetrahydrofuran; and (c) isolating the 6-O-methylerythromycin A form 0 solvate.

In yet another embodiment, the present invention provides 6-O-methylerythromycin A form 0-ethanolate prepared according to the foregoing process.

In yet another embodiment, the present invention provides 6-O-methylerythromycin A form 0-isopropyl acetate prepared according to the foregoing process.

In yet another embodiment, the present invention provides 6-O-methylerythromycin A form 0-tetrahydrofuran prepared according to the foregoing process.

In yet another embodiment, the present invention provides 6-O-methylerythromycin A form 0-isopropanolate prepared according to the foregoing process.

In yet another embodiment, the present invention provides a composition comprising from about 25% to about 95% of 6-O-methylerythromycin A form 0 solvate and from about 5% to about 75% of a carbomer.

In yet another embodiment, the present invention provides a method of treating bacterial infections in a host mammal in need of such treatment comprising administering to the mammal a therapeutically effective amount of 6-O-methylerythromycin A form 0 solvate-carbomer complex.

In yet another embodiment, the present invention provides a suspension for oral administration comprising 6-O-methylerythromycin form 0 solvate-carbomer complex suspended in a pharmaceutically acceptable liquid medium.

In yet another embodiment, the present invention provides a process for the preparation of 6-O-methylerythromycin A form 0 solvate-carbomer complex of from about 25% to about 95% of 6-O-methylerythromycin A form 0 solvate and from about 5% to about 75% of a carbomer comprising (a) dispersing a carbomer in an organic solvent; and (b) mixing the dispersion of step (a) with 6-O-methylerythromycin form 0 solvate to allow formation of the reaction product.

In yet another embodiment, the present invention provides 6-O-methylerythromycin A form 0 solvate-carbomer complex prepared according to the foregoing process.

In yet another embodiment, the present invention provides a process for the preparation of 6-O-methylerythromycin A form I comprising drying 6-O-methylerythromycin A form 0 solvate at a temperature of from about 0° C. to about 50° C.

In yet another embodiment, the present invention provides a process for the preparation of 6-O-methylerythromycin A form II comprising heating 6-O-methylerythromycin A form 0 solvate under vacuum at a temperature of between about 70° C. and 110° C.

DETAILED DESCRIPTION

6-O-methylerythromycin A is prepared by methylation of the 6-hydroxy group of erythromycin A. However, in addition to the 6 position, erythromycin A contains hydroxy groups at the 11, 12, 2' and 4" positions, and a nitrogen at 3' position, all of which are potentially reactive with alkylating agents. Therefore, it is necessary to protect the various reactive functionalities prior to alkylation of the 6 hydroxy group. Representative 6-O-methylerythromycin A preparations are described in U.S. Pat. Nos. 4,331,803, 4,670,549, 4,672,109 and 4,990,602 and European Patent Specification 260 938 B1 which are incorporated herein by reference. Following final removal of the protecting groups, the 6-O-methylerythromycin A may exist as a solid, a semisolid, or a syrup containing residual solvents from the deprotection reactions, inorganic salts, and other impurities. 6-O-methylerythromycin A form 0 solvate may be crystallized directly from the syrup or semisolid using the solvents listed above. Alternatively, if the crude reaction product solidifies, the solid may be recrystallized from any of the solvents described above. Pure 6-O-methylerythromycin A form 0 solvate may also be obtained by recrystallizing form II or mixtures of form I and form II from any of the solvents described above. The term "6-O-methylerythromycin A" as used herein is meant to include 6-O-methylerythromycin A in any crystalline form or mixtures thereof, as well as amorphous solids, syrups, or semisolids comprising 6-O-methylerythromycin A in any state of purity.

The term "treating" refers to crystallizing or recrystallizing 6-O-methylerythromycin A as defined above from any of the solvents described above.

6-O-methylerythromycin A is prepared from erythromycin A by a variety of synthetic routes. In one method, erythromycin A is converted to 2'-O-3'-N-bis (benzyloxycarbonyl)-N-demethylerythromycin A (I).

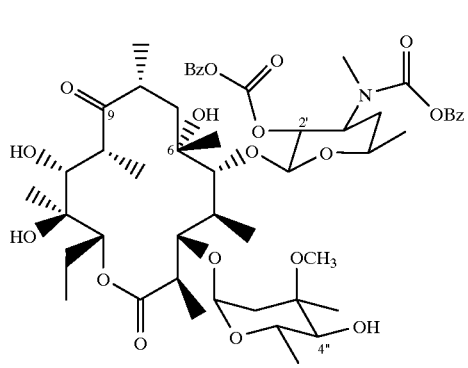

The 6-hydroxy group is then methylated by reaction with an alkylating agent such as bromomethane or iodomethane and a base. Removal of the benzoyl groups by catalytic hydrogenation and reductive methylation of the 3' N gives 6-O-methylerythromycin A. See U.S. Pat. No. 4,331,803.

An alternative synthetic route involves methylation of 6-O-methylerythromycin A-9-oxime. 6-O-methylerythromycin A-9-oxime is prepared by methods well known in the art such as reaction of erythromycin A with hydroxylamine hydrochloride in the presence of base, or by reaction with hydroxylamine in the presence of acid as described in U.S. Pat. No. 5,274,085. Reaction of the oxime with RX wherein R is allyl or benzyl and X is halogen results in formation of 2'-O,3'-N-diallyl or dibenzylerythromycin A-9-O-allyl or benzyloxime halide. Methylation of this quaternary salt as described above, followed by elimination of the R groups and deoxmimation gives 6-O-methylerythromycin A. See U.S. Pat. No. 4,670,549.

Methylation of 6-O-methylerythromycin A oxime derivatives of formula II,

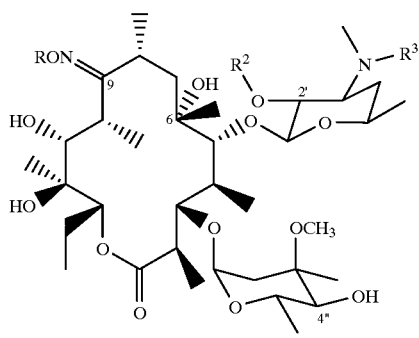

wherein R is alkyl, alkenyl, substituted or unsubstituted benzyl, oxyalkyl, or substituted plenylthioalkyl, $R^2$ is benzoyl, and $R^3$ is methyl or benzoyl, followed by deprotection, deoximation, and reductive methylation when $R^3$ is benzoyl gives 6-O-methylerythromycin A. See U.S. Pat. No. 4,672,109.

A particularly useful preparation of 6-O-methylerythromycin A involves methylation of the oxime derivative III,

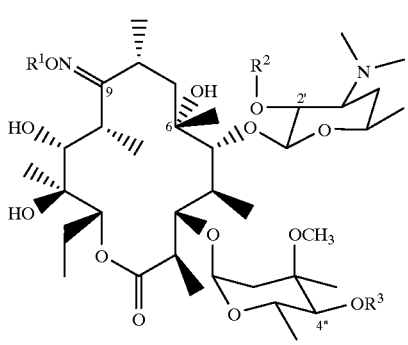

wherein $R^1$ is alkenyl, substituted or unsubstituted benzyl, or alkoxyalkyl, $R^2$ is substituted silyl, and $R^3$ is $R^2$ or H. Removal of the protecting groups and deoximation is then accomplished in a single step by treatment with acid to give 6-O-methylerythromycin A. See European Patent Specification 260 938 B1 and U.S. Pat. No. 4,990,602.

A preferred route ot 6-O-methylerythromycin A is outlined in Scheme 1. Erythromycin A, prepared by fermentation of *Streptomyces erythreus* is oximated to give oxime 4 wherein $R^1$ is alkoxyalkyl. The group $R^1$ may be introduced by reaction of erythromycin A with the substituted hydroxylamine $R^1ONH_2$, or by reaction of erythromycin A with hydroxylamine hydrochloride in the presence of base, or hydroxylamine in the presence of acid, followed by reaction with $R^1X$. The two hydroxy groups are then protected simultaneously, in which $R^2$ or $R^3$ are the same, or sequentially in which $R^2$ and $R^3$ are different. Particularly useful protecting groups are substituted silyl groups such as trimethylsilyl, tert-butyldimethylsilyl, tert-butyldiphenylsilyl and the like. The protecting groups are then removed and the compound is deoximated to produce 6-O-methylerythromycin A. The order of deprotection/deoxmation is not critical. When the protecting groups are substituted silyl, deprotection and deoximation can be accomplished in a single step by treatment with acid, for example using formic acid or sodium hydrogen sulfite. See U.S. Pat. No. 4,990,602.

Scheme 1

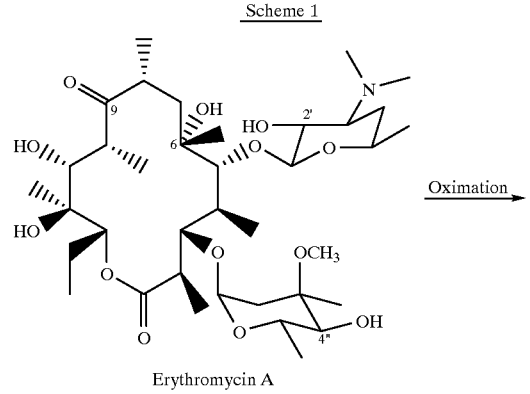

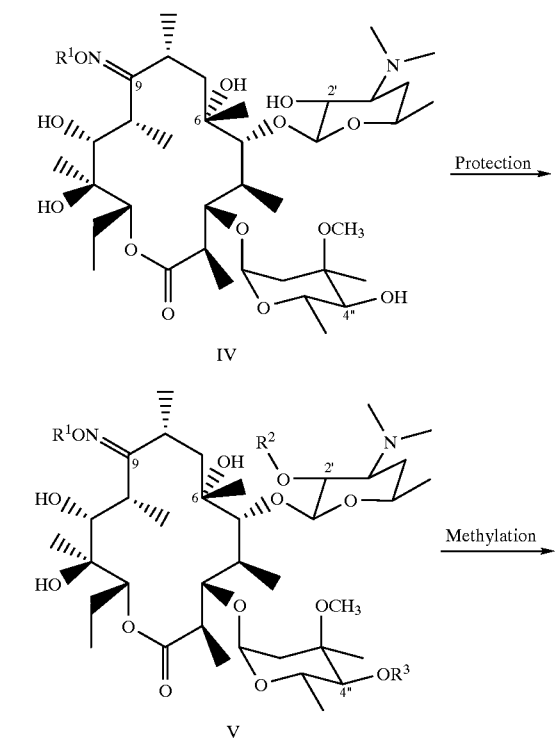

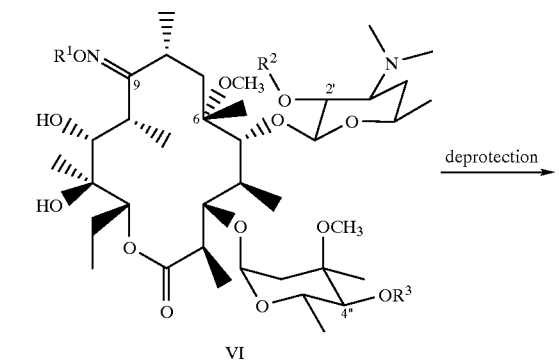

-continued

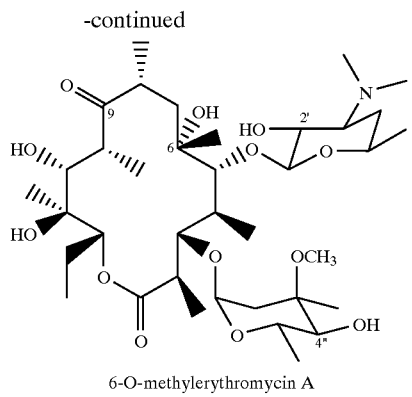

6-O-methylerythromycin A

In accordance with the process aspects of the present invention, 6-O-methylerythromycin A prepared by any of the methods described above is suspended in the desired solvent and heated to about the reflux temperature of the solvent. Heating is then continued and the suspension is stirred for an amount of time sufficient to dissolve most of the solid, generally about 10 minutes to 2 hours. The suspension is then filtered hot. If necessary, the filtrate may be heated to at or about the reflux temperature of the solvent to form a clear solution. The filtrate is then slowly cooled to ambient temperature with optional further cooling in an ice-water bath. For purposes of this specification, ambient temperature is from about 20 to about 25° C. 6-O-methylerythromycin A form 0 solvate is then isolated, preferably by filtration, and the wet crystals are transferred to a sealed container.

The most preferred solvent for the isolation of 6-O-methylerythromycin A form 0 solvate is ethanol.

6-O-methylerythromycin A form 0 solvate-carbomer complexes are prepared by dispersing from about 5% to about 75% by weight of a carbomer in an organic solvent and mixing the dispersion with from about 95% to about 5% of 6-O-methylerythromycin A form 0 solvate. A preferred organic solvent is acetone. The mixture is then stirred for a period of time sufficient to allow formation of the antibiotic-carbomer complex, generally from about 0.5 to about 12 hours. The solid complex is then isolated, preferably by filtration. If necessary, water may be added to the mixture to promote precipitation of the complex. The collected precipitate is then dried and milled to the desired particle size by conventional methods.

Alternatively, the carbomer complex may be prepared by mixing 6-O-methylerythromycin A form 0 solvate and the dry carbomer in a limited amount of organic solvent The solvent is then removed by evaporation, thereby eliminating the filtration step.

The carbomers employed in the foregoing process are branched acrylic acid polymers with a high degree of cross linking and thickening capacity. They have the general formula

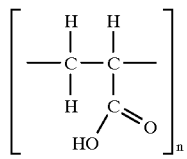

where n is from about 10,000 to about 60,000. The average equivalent weight is 76, while the molecular weight is approximately 3 million. A preferred material is in the U.S. Pharmacopoeia as Carbomer 934P. This carbomer is classified as a water soluble resin and has been used in other pharmaceutical compositions for its thickening and suspending properties. In its presolvated state, the carbomer is a tightly coiled molecule and its thickening properties are limited. However, due to its relatively high molecular weight and extensive resin cross linking, the carbomer can generate a high viscosity gel. This gelation is initially believed to occur as a result of hydration and partial uncoiling. Neutralization of the acidic groups of the carbomer with a suitable base organic or inorganic base is required to further uncoil the molecule and generate high viscosity solutions.

The term "6-O-methylerythromycin A form 0 solvate-carbomer complex or granule" refers to the product obtained in the above process. While not intending to be limited by theory, the granule is believed to be held together by both ionic attraction between the amino group of 6-O-methylerythromycin A form 0 solvate and the carbonyl group of the carbomer, and the gel properties of the carbomer.

The antibiotic-carbomer complexes of this invention can be employed in dry form, preferably in the form of particles. Such particles can be mixed with foods or beverages, can be used to prepare liquid suspensions for oral administration, or can be formed into conventional whole or chewable tablets for oral administration.

In such solid dosage forms, the antibiotic-carbomer complex is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. The dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms can be prepared with coatings and shells such as enteric coatings and other coatings well known in the pharmaceutical formulating art They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Suspensions for oral administration may contain, in addition to the antibiotic-carbomer complex, inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3- butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Preferably, fine particles having average diameters smaller than 40 mesh (420 microns) will be employed. For use in a pediatric suspension a mean particle diameter of less than 50 mesh (297 microns) will be desirable. In some products, the particles will be larger, having a mean diameter of less than 10 mesh (2000 microns), or more preferably less than 1000 microns (about 16 mesh).

To further reduce dissolution of the active drug in the mouth, the complexes provided in accordance with the present invention can be polymer coated. A variety of polymeric materials can be employed. Non-limiting examples of such materials include ethyl cellulose, hydroxypropyl cellulose, hydroxypropylmethyl cellulose, polyvinyl acetate phthalate, cellulose acetate phthalate, hydroxypropylmethyl cellulose phthalate and shellac, as well as numerous other polymers familiar to those of ordinary skill in the pharmaceutical arts. Such other polymers commonly known by tradenames include Eudragit® E-100, S-100 and L-100 polymers, available from the Rohm and Haas Company. Most preferable is hydroxypropylmethyl cellulose phthalate.

The use of pH sensitive coatings offer advantages in addition to taste coverage. A coating insoluble at neutral pH, but soluble in acid (e.g. Eudragit® E-100) can give complete taste coverage in the neutral pH of the mouth, while still allowing rapid dissolution in the strongly acidic stomach contents after swallowing. Conversely, an enteric coating can be insoluble in acid or water while dissolving rapidly in a neutral buffer above pH 5 or 6. This offers the opportunity to prepare a suspension of antibiotic-carbomer complex that remains intact in the formulation but rapidly releases the antibiotic in the intestine. The drug thereby remains protected from the hostile environment of the stomach, but are rapidly dissolved in the higher pH of the intestinal tract.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 1000, more preferably of about 5 to about 200 mg of 6-O-methylerythromysin A form 0 solvate per kilogram of body weight per day are administered to a mammalian patient If desired, the effective daily dose may be divided into multiple doses for purposes of administration, e.g. two to four separate doses per day.

The following Examples are provided to enable one skilled in the art to practice the invention and are merely illustrative of the invention. They should not be read as limiting the scope of the invention as defined in the claims.

EXAMPLE 1

Preparation of 6-O-methylerythromycin Form 0.Ethanolate

6-O-methylerythromycin A was prepared from erythromycin A by oximation of the C-9 carbonyl, protection of the C-2' and C-4" hydroxy groups, methylation of the C-6 hydroxy group, deoximation and removal of the protecting groups, and recrystallization from ethanol according to the method of U.S. Pat. No. 4,990,602.

A mixture of 6-O-methylerythromycin A (20 g), prepared as described above, and ethanol (200 mL) was warmed to reflux and the insoluble material (11.2 g) was removed by filtration. The filtrate was transferred to a clean flask and heated to reflux. The clear solution was allowed to cool to ambient temperature and then was further cooled in an ice bath. The liquid was decanted to leave 6-O-methylerythromycin A form 0 ethanolate which was sealed in a container without further drying. The 2-theta angle positions in the single crystal x-ray diffraction pattern of 6-O-methylerythromycin A form 0-ethanolate are 4.72°±0.2, 6.60°±0.2, 7.72°±0.2, 9.30°±0.2, 10.40°±0.2, 11.10°±0.2, 11.86°±0.2, 12.72°±0.2, 13.90°±0.2, 15.02°±0.2, 17.18°±0.2, 18.50°±0.2, 19.08°±0.2, 19.68°±0.2, 23.14°±0.2 and 23.98°±0.2.

EXAMPLE 2

Preparation of 6-O-methylerythromycin Form 0.Isopropyl Acetate

A mixture of 6-O-methylerythromycin A (10 g), prepared as described in Example 1, and isopropyl acetate (100 mL) was warmed to 73° C. The hot solution was filtered to remove traces of insoluble material. The clear solution was then cooled slowly to ambient temperature. The liquid was decanted and the wet solid sealed in a container without further drying.

The 2-theta angle positions in the single crystal x-ray diffraction pattern of 6-O-methylerythromycin A form 0.Isopropyl Acetate are 4.76°±0.2, 6.70°±0.2, 7.80°±0.2, 9.128°±0.2, 10.56°±0.2, 11.96°±0.2, 12.24°±0.2, 12.36°±0.2, 12.60°±0.2, 12.84°±0.2, 13.96°±0.2, 15.16°±0.2, 16.68°±0.2, 17.28°±0.2, 18.52°±0.2, 19.18°±0.2, 19.80°±0.2, 20.56°±0.2, 21.52°±0.2 and 23.96°±0.2.

EXAMPLE 3

Preparation of 6-O-methylerythromycin Form 0.Tetrahydrofuran

A mixture of 6-O-methylerythromycin A (10 g), prepared as described in Example 1, and tetrahydrofuran (20 mL) was warmed to 50° C. The hot solution was filtered and the filtrate was cooled slowly to ambient temperture. The liquid was decanted and the wet solid sealed in a container without further drying.

EXAMPLE 4

Preparation of 6-O-methylerythromycin Form 0.isopropanolate

A mixture of 6-O-methylerythromycin A (5 g), prepared as described in Example 1, and isopropanol (20 mL) was warmed to 60° C. The hot solution was gravity filtered to give 10 mL of clear filtrate which was cooled slowly to ambient temperature. The liquid was decanted and the wet solid sealed in a container without further drying.

EXAMPLE 5

Conversion of 6-O-methylerythromycin A form 0 solvate to 6-O-methylerythromycin A form I.

6-O-methylerythromycin A form 0 solvate prepared as in Examples 1–4 is dried in a vacuum oven (40–45° C., 4–8 in. Hg) to give 6-O-methylerythromycin A form I. The 2-theta angle positions in the powder x-ray diffraction pattern of 6-O-methylerythromycin A form I are 5.16°±0.2, 6.68°±0.2, 10.20°±0.2, 12.28°±0.2, 14.20°±0.2, 15.40°±0.2, 15.72°±0.2, and 16.36°±0.2.

EXAMPLE 6

Conversion of 6-O-methylerythromycin A form 0 solvate to 6-O-methylerythromycin A form II.

6-O-methylerythromycin A form 0 solvate, prepared as in Examples 1–4, is placed in a vial and heated in the vacuum oven (4–9 in Hg, 100–110° C.) for 18 hours to give 6-O-methylerythromycin A form II crystals. 6-O-methylerythromycin A form II melts at 223.4° C. The 2-theta angle positions in the powder x-ray diffraction pattern of 6-O-methylerythromycin A form II are 8.52°±0.2, 9.48°±0.2, 10.84°±0.2, 11.48°±0.2, 11.88°±0.2, 12.36°±0.2, 13.72°±0.2, 14.12°±0.2, 15.16°±0.2, 16.48°±0.2, 16.92°±0.2, 17.32°±0.2, 18.08°±0.2, 18.40°±0.2, 19.04°±0.2, 19.88°±0.2, and 20.48°±0.2.

EXAMPLE 7

Preparation of 6-O-methylerythromycin A form 0-carbomer complex

The desired complex is prepared by stirring a mixture in acetone of about 1.5 parts by weight of 6-O-methylerythromycin form 0.ethanolate and 1 part by weight of Carbomer 934P until the mixture is uniform. Water is then added with stirring and the resulting precipitate is stirred for about 30 minutes. The solids are separated by vacuum filtration and washed with water. The damp filter cake is then passed through a 30 mesh screen and dried in a vacuum oven at about 40° C. The potency of the complex is determined by colorimetric analysis.

We claim:

1. An isolated crystalline antiobiotic designated 6-O-methylerythromycin A form 0 solvate having the structure

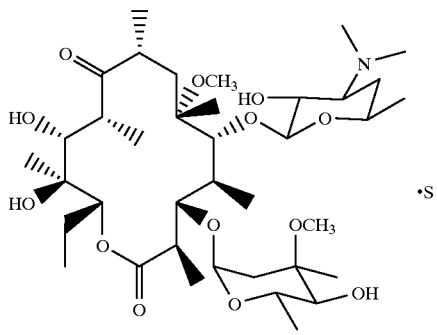

wherein S is a solvating molecule selected from the group consisting of ethanol, isopropyl acetate, isopropanol and tetrahydrofuran.

2. 6-O-methylerythromycin A form 0 solvate according to claim 1 characterized by 2-theta angle positions in the powder x-ray diffraction pattern of 4.581°±0.2, 6.498°±0.2, 7.615°±0.2, 9.169°±0.2, 10.154°±0.2, 11.009°±0.2, 11.618°±0.2, 12.495°±0.2, 13.772°±0.2, 14.820°±0.2, 16.984°±0.2, 18.221°±0.2, 18.914°±0.2 and 19.495°±0.2.

3. A crystalline antibiotic according to claim 1 having the name 6-O-methylerythromycin A form 0.ethanolate characterized by 2-theta angle positions in the powder x-ray diffraction pattern of 4.72°±0.2, 6.60°±0.2, 7.72°±0.2, 9.30°±0.2, 10.40°±0.2, 11.10°±0.2, 11.86°±0.2, 12.72°±0.2, 13.90°±0.2, 15.02°±0.2, 17.18°±0.2, 18.50°±0.2, 19.08°±0.2, 19.68°±0.2, 23.14°±0.2 and 23.98°±0.2.

4. A crystalline antibiotic according to claim 1 having the name 6-O-methylerythromycin A form 0.isopropyl acetate characterized by 2-theta angle positions in the powder x-ray diffraction pattern of 4.76°±0.2, 6.70°±0.2, 7.80°±0.2, 9.128°±0.2, 10.56°±0.2, 11.96°±0.2, 12.24°±0.2, 12.36°±0.2, 12.60°±0.2, 12.84°±0.2, 13.96°±0.2, 15.16°±0.2, 16.68°±0.2, 17.28°±0.2, 18.52°±0.2, 19.18°±0.2, 19.80°±0.2, 20.56°±0.2, 21.52°±0.2 and 23.96°±0.2.

5. A crystalline antibiotic according to claim 1 having the name 6-O-methylerythromycin A form 0.tetrahydrofuran.

6. A crystalline antibiotic according to claim 1 having the name 6-O-methylerythromycin A form 0.isopropanolate.

7. A composition comprising a therapeutically effective amount of an isolated 6-O-methylerythromycin A form 0 solvate in combination with a pharmaceutically acceptable carrier.

8. A method of treating bacterial infections in a host mammal in need of such treatment comprising administering to the mammal a therapeutically effective amount of an isolated 6-O-methylerythromycin A form 0 solvate.

9. A process for preparing 6-O-methylerythromycin A form 0 solvate comprising (a) converting erythromycin A to 6-O-methylerythromycin A;

(b) treating the 6-O-methylerythromycin prepared in step a with a solvent selected from the group consisting of ethanol, isopropyl acetate, isopropanol, and tetrahydrofuran; and (c) isolating the 6-O-methylerythromycin form 0 solvate crystals.

10. The process of claim 9 wherein step (a) comprises (i) converting erythromycin A into an erythromycin A 9-oxime derivative;

(ii) protecting the 2' and 4" hydroxy groups of the erythromycin A 9-oxime derivative prepared in step i;

(iii) reacting the product of step ii with a methylating agent;

(iv) deprotecting and deoximating the product of step iii to form 6-O-methylerythromycin A.

11. The process of claim 10 wherein the solvent is ethanol.

12. 6-O-methylerythromycin form 0-ethanolate prepared according to the process of claim 11.

13. The process of claim 10 wherein the solvent is isopropyl acetate.

14. 6-O-methylerythromycin form 0.isopropyl acetate prepared according to the process of claim 13.

15. The process of claim 10 wherein the solvent is isopropanol.

16. 6-O-methylerythromycin form 0.isopropanolate prepared according to the process of claim 15.

17. The process of claim 10 wherein the solvent is tetrahydrofuran.

18. 6-O-methylerythromycin form 0.tetrahydrofuran prepared according to the process of claim 17.

19. A complex comprising from about 25% to about 95% of an isolated crystalline antibiotic designated 6-O-methylerythromycin A form 0 solvate having the structure

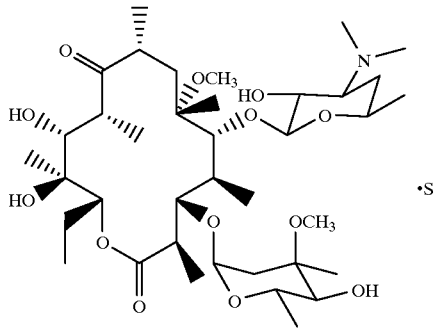

wherein S is a solvating molecule selected from the group consisting of ethanol, isopropyl acetate, isopropanol and tetrahydrofuran and from about 5% to about 75% of a carbomer.

20. A method of treating bacterial infections in a host mammal in need of such treatment comprising administering to the mammal a therapeutically effective amount of the complex of claim 19.

21. A suspension for oral administration comprising the complex of claim 19 suspended in a pharmaceutically acceptable inert diluent.

22. A process for the preparation of 6-O-methylerythromycin A form 0 solvate-carbomer complex of from about 25% to about 95% of an isolated crystalline antibiotic designated 6-O-methylerythromycin A form 0 solvate having the structure

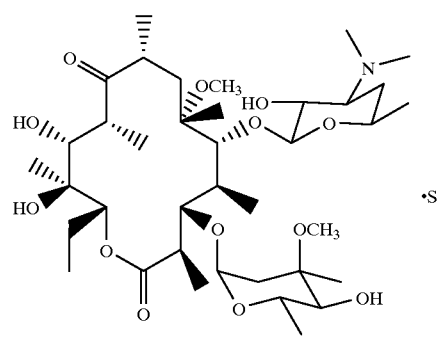

wherein S is a solvating molecule selected from the group consisting of ethanol, isopropyl acetate, isopropanol and tetrahydrofuran and from about 5% to about 75% of a carbomer comprising (a) dispersing a carbomer in an organic solvent; and (b) mixing the dispersion of step (a) with 6-O-methylerythromycin form 0 solvate to allow formation of the reaction product.

23. 6-O-methylerythromycin A form 0 solvate-carbomer complex prepared according to the process of claim 22.

24. A process for the preparation of 6-O-methylerythromycin A form I comprising drying an isolated 6-O-methylerythromycin A form 0 solvate at a temperature of from about 0° C. to about 50° C.

25. A process for the preparation of 6-O-methylerythromycin A form II comprising heating an isolated 6-O-methylerythromycin A form 0 solvate under vacuum at a temperature of between about 70° C. and 110° C.

* * * * *